(12) United States Patent
van Krieken et al.

(10) Patent No.: US 7,705,180 B2
(45) Date of Patent: Apr. 27, 2010

(54) PROCESS FOR THE PREPARATION OF LACTIC ACID OR LACTATE FROM A MAGNESIUM LACTATE COMPRISING MEDIUM

(75) Inventors: Jan van Krieken, Gorinchem (NL); Roelf Otto, Gorinchem (NL); Gerrit Leendert Nanninga, Giessen (NL); Johannes Jeichinus de Vries, Dalem (NL)

(73) Assignee: Purac Biochem B.V., Gorinchem (NL)

( * ) Notice: Subject to any disclaimer, the term of this patent is extended or adjusted under 35 U.S.C. 154(b) by 649 days.

(21) Appl. No.: 11/153,465

(22) Filed: Jun. 16, 2005

(65) Prior Publication Data
US 2005/0281913 A1 Dec. 22, 2005

Related U.S. Application Data

(60) Provisional application No. 60/580,228, filed on Jun. 17, 2004.

(51) Int. Cl.
*C07C 59/00* (2006.01)
*C07C 59/08* (2006.01)
(52) U.S. Cl. ........................................ 562/589; 562/579
(58) Field of Classification Search .................. None
See application file for complete search history.

(56) References Cited

U.S. PATENT DOCUMENTS 1,459,395 A 6/1923 Hamburger 3,429,777 A 2/1969 Bode

FOREIGN PATENT DOCUMENTS

| GB | 173479 | | 11/1922 |
| JP | B4-63000038 | | 1/1988 |
| NL | A-288829 | | 2/1962 |
| WO | 9822611 | * | 5/1998 |
| WO | WO 98/22611 | | 5/1998 |
| WO | 199837050 | * | 8/1998 |
| WO | WO 98/37050 | | 8/1998 |
| WO | WO 00/17378 | | 3/2000 |

OTHER PUBLICATIONS

The Merck Index, 12$^{th}$ edition 1996, Merck Research Laboratories, Whitehouse Station, NJ, XP002309717, p. 969, col. 2, entry Mg(OH)2.
English abstract of Czech Patent No. CZ 279449, Apr. 12, 1995.
English abstract of Zbiobrowsky, Jerzy; Lesniak Wladyslaw, Przemysl refment, (1964), 7(1), 3-6.

* cited by examiner

*Primary Examiner*—Karl J Puttlitz
(74) *Attorney, Agent, or Firm*—Oliff & Berridge, PLC

(57) ABSTRACT

The present invention relates to an improved process for the preparation of lactic acid and or lactate from a magnesium lactate comprising medium. In said process, magnesium lactate is reacted with a hydroxide of sodium, calcium, and/or ammonium at a pH range between 9 and 12, preferably between 9.9 and 11, to form a lactate of sodium, potassium, calcium and/or ammonia and magnesium hydroxide. With the process according to the invention a lactate salt is formed and magnesium hydroxide. It is essential that said so-called SWAP reaction is conducted within a specific pH range: It was found that when conducting the SWAP reaction at a pH range between 9 and 12 magnesium hydroxide particles are formed which can easily be separated from the lactate salt solution formed.

26 Claims, No Drawings

PROCESS FOR THE PREPARATION OF LACTIC ACID OR LACTATE FROM A MAGNESIUM LACTATE COMPRISING MEDIUM

This nonprovisional application claims the benefit of U.S. Provisional Application No. 60/580,228, filed Jun. 17, 2004.

The present invention relates to an improved process for the preparation of lactic acid and or lactate from a magnesium lactate comprising medium.

Lactic acid (LA) is a hydroxy acid used primarily in the food industry. It is also used in the polymer industry for the preparation of polylactic acid, which is a biodegradable polymer.

Most of the commercial processes for the preparation of lactic acid are based on the fermentation of carbohydrates by micro-organisms. These processes require strict control of temperature and pH. A common feature to all the fermentation processes is the need to neutralize the acids excreted by the micro-organisms in the process. A drop in pH below a critical value, depending on the micro-organism used in the process, could damage the micro-organism's metabolic process and bring the fermentation process to a stop. Therefore, it is common practice to add $Ca(OH)_2$ to the fermentation reaction and thus produce calcium lactate. The use of sulphuric acid to liberate lactic acid from calcium lactate subsequently generates calcium sulphate as solid waste, which is currently disposed as gypsum. An increase in the production of lactic acid will generate a substantial increase in solid waste, which could eventually become an unbearable burden to the environment. In addition to this, and in spite of the various separation schemes developed for fermentation processes, the separation of LA of high purity still remains an elusive goal. An example of a process for the preparation of lactic acid using a calcium base as neutralising agent is described in WO 98/22611. This patent publication describes a process for producing lactic acid, wherein lactic acid is produced by fermentation, adding alkaline earth base such as calcium base to form alkaline earth lactate such as calcium lactate, removing biomass, reacting the alkaline earth base with an ammonium source to form ammonium lactate, and recovering lactic acid therefrom by salt splitting electrodialysis. If the desired product is a specific lactate salt, with conventional processes a calcium lactate salt resulting from the fermentation with calcium base as a neutralising agent is prepared first. Then the calcium lactate is converted into lactic acid by means of sulphuric acid addition under formation of gypsum, and subsequently the lactic acid is converted into the lactate salt desired. It goes without saying that this process for preparing lactate salt is laborious, time-consuming, and results in unwanted solid waste in the form of gypsum.

It is a purpose of the present invention to provide an improved process for the production of lactic acid and/or lactate salt.

It is a further purpose of the invention to provide an environmentally friendly process for the preparation of lactic acid and/or lactate salt.

It is another purpose of the invention to provide a process for the preparation of lactic acid and/or lactate salt, comprising an improved separation process.

Other objects of the invention will become apparent as the description proceeds.

According to the present invention lactic acid and/or lactate salt is prepared via an improved process comprising an improved separation stage. Said process may be conducted virtually free of any solid or liquid waste effluents, hence being environmentally friendly. The present invention provides a process for the preparation of lactic acid and/or lactate from a medium comprising magnesium lactate.

In the prior art, several publications describe the possibility of using a magnesium base for neutralising agent in lactic acid fermentations:

*Magnesium carbonate as a neutralising agent for the lactic acid formed during fermentation of sugare mashes*, Zbiobrowsky, Jerzy; Lesniak Wladyslaw, Przemysl refment, (1964), 7(1), 3-6 describes the use of magnesium carbonate as neutralising agent for lactic acid produced in fermentation of molasses and white sugar. The magnesium lactate is converted into magnesium carbonate and sodium lactate over an ion exchange column.

Also JP-B4-63000038 is directed to the lactic acid recovery from a fermentation broth by converting the acid into its magnesium salt and evaporation at a temperature above 50° C. This resulted in crystalline magnesium lactate, which was converted into lactic acid with an ion-exchange resin.

*Manufacture of magnesium lactate*, Kolomaznik, A. Blaha, S. Saha, L. Saha, Czech Rep. CZ 279, 449, 12 Apr. 1995 is directed to the production of magnesium lactate by fermentation of wey (lactose) and neutralisation with magnesium oxide, hydroxide or carbonate.

The conversion, at pH 4.5-5.0 was significantly higher than in the presence of conventional Ca-bases.

U.S. Pat. No. 1,459,395 describes the purification of lactic acid by neutralization of commercial (dark) lactic acid with magnesium oxide, hydroxide or carbonate to produce magnesium lactate. The magnesium lactate is acidulated with concentrated sulphuric acid in a suitable solvent. After removing the magnesium sulphate by filtration the resulting solution is distilled to remove solvent. The pure lactic acid remains as a residue. Also a conversion from calcium lactate to magnesium lactate with the formation of calcium sulphate (a so-called SWAP reaction) is mentioned.

GB 173,479 describes a process for the purification of lactic acid from fermentation in which the lactic acid in solution is converted into magnesium lactate. The lactic acid in solution may be converted into a more soluble lactate salt such as calcium lactate prior to its conversion to magnesium lactate. The resulting magnesium lactate solution is acidified with sulphuric acid and the lactic acid is recovered by extraction with, for instance, acetone. The extraction and acidulation step may also be combined by suspending the magnesium salt solution in acetone and then acidifying to form precipitated magnesium sulphate and lactic acid.

WO 00/17378 is directed to the fermentation of sugar to form lactic acid. The pH of the fermentation broth is adjusted to 5.5 to 6.5 by addition of calcium or magnesium hydroxide. The magnesium lactate is converted with hydrochloric acid to form lactic acid and magnesium chloride. The lactic acid is extracted by LLE with isoamylalcohol, an amine or an ether. The magnesium chloride is decomposed thermally to hydrochloric acid and magnesium oxide.

In a second embodiment the fermentation broth (after separation of the biomass) is concentrated to allow magnesium or calcium lactate precipitation. The precipitate is acidified with HCl. It is indicated that the fermentation broth typically contains about 5 to 6 wt. % magnesium or calcium lactate, calculated as lactic acid and that said concentration is insufficient for crystallization at ambient temperature. Therefore the broth is concentrated to about 15 wt. %, upon cooling of the concentrated broth precipitation occurs.

U.S. Pat. No. 3,429,777 describes the production of magnesium lactate from a crude lactic acid solution with soluble proteins and soluble phosphates. Said crude lactic acid solution is defined as crude lactate incubated steepwater liquor or crude sugar liquor such as molasses. The lactic acid is recovered by either sulphuric acid or phosphoric acid acidulation, optionally in combination with $CO_2$. Also the possibility of converting the magnesium lactate to sodium lactate by the addition of soda ash, caustic soda or sodium phosphate to a magnesium lactate solution to produce sodium lactate and magnesium carbonate or magnesium hydroxide was mentioned. However, no details are provided on how to conduct this process and under which conditions.

NL-A-288829 describes the continuous fermentation of sugars to form lactic acid, wherein magnesium or zinc salt is added continuously to set the pH and to form magnesium lactate or zinc lactate, which is periodically removed by filtration from the fermentation broth under simultaneous addition of sugar.

WO 98/37050 (Eyal) describes the preparation of lactic acid from a (fermentation) medium containing alkaline earth-metal salt of lactic acid comprising:

a) reacting the alkaline earth metal salt of lactic acid with an alkaline metal base to form alkaline metal salt of lactic acid and alkaline earth metal base, b) separation said alkaline earth metal salt from the alkali metal salt of lactic acid, c) splitting the alkali metal salt of lactic acid into lactic acid and alkali metal salt, d) separation said lactic acid and alkali metal salt, either by filtering or extraction.

e) recycling the alkali metal salt to step (a), and, f) recycling the alkaline earth metal salt isolated in step (b) to the (fermentation) medium.

The alkaline earth metal salt of lactic acid may be the calcium salt of lactic acid or the magnesium salt of lactic acid. The alkali metal salt preferably is a sodium or potassium salt preferably hydroxides, carbonates or bicarbonates thereof. The salt splitting step may be electrodialytic salt splitting.

Although the whole process is clearly directed to the use of calcium base as a neutralising agent, the use of a magnesium base is mentioned as an alternative. The publication further indicates that the alkaline-earth metal lactate may be converted into a sodium or potassium lactate by a SWAP-step. To this end a Na/K base such as hydroxide, oxide carbonate, bicarbonate is added to the alkaline-earth metal lactate. Because of the low solubility of calcium carbonate, the use of bicarbonates is preferred. For said SWAP with calcium lactate and sodium bicarbonate a pH between 5 and 10, more preferably between 7 and 9, is preferred. As the solubilities (and other physical and chemical properties) of the various calcium bases substantially differ from the various magnesium-bases (also relatively to each other, e.g. calcium hydroxide is more soluble than calcium carbonate while magnesium carbonate is more soluble than magnesium hydroxide), the teachings of Eyal (which are clearly directed to and based on calcium and (bi)carbonate only) cannot be used for magnesium-based SWAP processes.

Although the use of magnesium base for neutralising agent in lactic acid fermentations is known, none of the abovementioned publications fully acknowledge the advantageous properties of magnesium lactate compared with compounds such as calcium lactate and other lactate salts formed when using other neutralising agents. Nor are these advantageous properties utilized for developing an environmental-friendly process with improved purification and separation of lactic acid and/or lactate. Further, none of the publications mentioned above teach the reaction conditions necessary for such a process. For optimally making use of all the advantages that magnesium has as a neutralising agent for lactic acid fermentations, it should be possible to readily isolate the lactic acid or lactate formed from the magnesium lactate from its by-products. Preferably the by-products should be recyclable, so as to obtain a process which can be conducted virtually free of any solid or liquid waste effluents, hence being environmentally friendly.

To this end, the present invention is directed to a process for the preparation of lactic acid and/or lactate from a medium comprising magnesium lactate, wherein the magnesium lactate is reacted with a hydroxide of sodium, potassium, calcium, and/or ammonium at a pH range between 9 and 12, preferably between 9.5 and 11, to form a lactate of sodium, potassium, calcium and/or ammonium and magnesium hydroxide.

With the process according to the invention a lactate salt is formed and magnesium hydroxide. It is essential that said so-called SWAP reaction is conducted within a specific pH range: It was found that when conducting the SWAP reaction at a pH range between 9 and 12 magnesium hydroxide particles are formed which have the right size and morphology to be easily separatable from the lactate salt solution formed. It was found that when, for instance, conducting a SWAP at a pH below 9 a gel-like layer of magnesium hydroxide is formed (even before all magnesium lactate is converted) which cannot be filtered. It was further found that conducting the SWAP reaction at a pH above 12 is not viable, because then porous, voluminous magnesium hydroxide particles are formed which form a magnesium hydroxide filter cake with a very low solid content. Further an excess base is present in the sodium lactate solution which has to be neutralised.

Optionally, the magnesium lactate (-containing medium) is pre-treated prior to the SWAP reaction according the invention. Especially when the magnesium lactate originates from the fermentation of carbohydrates, it may be advantageous to pre-treat said magnesium lactate (-containing medium) by biomass separation, washing, filtration, recrystallization or concentration, and combinations thereof, etcetera. When the magnesium lactate originates from the fermentation of carbohydrate, preferably the biomass is removed and the magnesium lactate is washed prior to the SWAP reaction. The washing step is preferably performed with water, which may be cold or heated. Biomass separation usually is conducted by means of filtration, flotation, sedimentation, centrifugation, flocculation and or combinations thereof.

With the process according to the invention magnesium lactate slurries can be used with relatively high concentrations; up to 38 wt. % magnesium lactate slurries (calculated as the anhydrate) can be suitably used. Cf. in the prior art about 20 wt. % calcium lactate slurries are subjected to a SWAP reaction, resulting in about 18 wt. % sodium lactate solutions. It should be noted that said magnesium lactate slurries comprise both magnesium lactate in suspension and in solution. Preferably, magnesium lactate slurries with concentration 8.5 to 30 wt. % (calculated as the anhydrate) are used, more preferably slurries with a concentration of 17 to 25 wt. %. This results in sodium, calcium, potassium and/or ammonium lactate solutions of high concentration. It was found that resulting lactate solutions with a concentration of up to 40 wt. % in the liquid part of the reaction medium could easily be handled within the process according to the invention. Preferably, the process is performed so that lactate is formed in a concentration of up to 30 wt. % in the liquid part of the reaction medium.

In order to ensure a homogenous reaction and the formation of magnesium hydroxide particles with optimal size and morphology, it is advised to conduct the SWAP reaction under intensive agitation. This can be done by means of conventional mixers and/or stirrers such as stirred tank reactors.

Also the reaction temperature is relevant for obtaining magnesium hydroxide particles with optimal particle size and morphology. Preferably, the process according to the invention is carried out at a temperature between 20 and 100° C., more preferably between 20 and 75° C.

When filtration is used for the separation of the magnesium hydroxide from the (liquid) sodium lactate, it was found that the separation time became too long when the reaction temperature was below 20° C., on the other hand when a temperature above 100° C. is used, the solid content of the filter cake becomes too low.

The process according to the invention is preferably carried out continuously.

In a preferred embodiment according to the invention, the reaction is carried out in two steps wherein in the first step magnesium lactate is reacted with a hydroxide of sodium, potassium, calcium, and/or ammonium at a pH range between 9 and 12, preferably between 9.5 and 11, to form a lactate of sodium, potassium, calcium and/or ammonium and magnesium hydroxide, and in a second step the pH is slightly increased to a pH between 10.5 and 12. Said second step ensures the removal of virtually all magnesium ions from the lactate. This is relevant for preparing a product with a low magnesium ion content. This can be necessary regarding product specifications or certain further processing steps such as membrane electrodialysis, which requires a very low magnesium content. Additional purification steps like ion exchange, might be necessary to reach the desired magnesium content.

As mentioned above, the magnesium hydroxide and the lactate salt formed can be easily separated from each other. The magnesium hydroxide particles can be separated by filtration or sedimentation. Preferably, the magnesium hydroxide formed is directly separated from the reaction medium, because at that point in time the particle size and morphology of the magnesium hydroxide particles are optimal. Optionally, the magnesium hydroxide particles are washed with water after separation. In the case of a continuous process the magnesium hydroxide particles are preferably continuously removed from the reaction medium. In the case of a batch process it is preferred that the magnesium hydroxide particles are removed from the reaction medium directly after formation or as soon as technically possible.

The magnesium hydroxide formed in the process according to the invention is very pure and may suitably be used for neutralising agent in fermentation of carbohydrates to form lactic acid.

It was found advantageous to, after separation of the magnesium hydroxide, submit the lactate of sodium, potassium, calcium and/or ammonium formed to a "pH correction step". In this step a small amount of acid is added to prepare a pH neutral product.

Although the product of the process according to the invention is relatively pure, after retrieval of the product, the lactate of sodium, potassium, calcium and/or ammonium may be subjected to one or more further purification/modification steps, such as activated carbon treatment, extraction, electrodialysis etcetera. These purification steps are known in the art and need no further elucidation here. The product of the process according to the invention may very suitably be subjected to a modification step wherein, for instance, the lactate is converted into lactic acid. This results in a lactic acid of very high purity. Said conversion may be conducted by means of bipolar electrodialysis or addition of a strong mineral acid.

The lactate of sodium, potassium, calcium and/or ammonium may also be converted into another lactate salt or lactate ester such as zinc lactate, ferrous lactate, ferric lactate, manganese lactate, aluminum lactate, ethyl lactate, ethyl hexyl lactate, butyl lactate, combinations thereof, etcetera.

The magnesium lactate comprising medium can easily be obtained from fermentation of carbohydrate to lactic acid. This can be a fermentation of carbohydrates to lactic acid wherein magnesium base is used as a neutralising agent, but also a fermentation can be used wherein the lactic acid formed is neutralised to form another lactate salt and said lactate salt (optionally via lactic acid conversion) is converted into magnesium lactate. It was found unnecessary to separate said other lactate salt from the fermentation broth prior to conversion to magnesium lactate. The magnesium lactate crystallises from the fermentation broth into clearly defined elongated block-shaped crystals. Owing to the slow crystallisation, inclusion of impurities in the magnesium lactate crystals hardly occurs and crystals with a clearly defined shape are formed. Thus, the crystallisation step inherently represents an efficient purification step. As with the process according to the invention the magnesium lactate can easily be converted into a very pure lactate in liquid form, which can easily be separated from the solid magnesium hydroxide formed, all advantages of using magnesium base as a neutralising agent are optimally utilized. One of the advantages of the process according to the invention is that a medium can be used which is relatively impure, while a relatively pure lactate is obtained. Thus any carbohydrate source can be used for the process according to the invention, even relatively raw carbohydrate sources can be used for the fermentation. Examples of suitable carbohydrate sources are sucrose, (liquefied) starch, sugar syrup etcetera. As mentioned-above, if the medium originates from the fermentation of carbohydrate it is advantageous to separate the biomass from the magnesium lactate (-containing medium) prior to reacting the magnesium lactate with a hydroxide of sodium, potassium, calcium and/or ammonium.

As mentioned above the magnesium hydroxide, which is formed during the reaction according to the invention is also very pure and can advantageously be used as neutralising agent in fermentation processes. Also for the above-mentioned fermentation, the magnesium hydroxide formed later in the process can be recycled into the fermentation as neutralising agent. No additional impurities are added and the single side-product (magnesium hydroxide) is recycled into the reaction, so that a so-called salt-less process is obtained. Thus the invention is further directed to a process for the preparation of lactic acid and/or lactate wherein:

a) a carbohydrate source is fermented to lactic acid and/or lactate in the presence of a micro-organism, b) magnesium hydroxide is used for neutralizing agent during the fermentation, c) a medium comprising magnesium lactate is formed, d) optionally, the medium comprising magnesium lactate is treated prior to, e) reacting magnesium lactate in the medium comprising magnesium lactate with a hydroxide of sodium, potassium, calcium, and/or ammonium at a pH range between 9 and 12, preferably between 9.5 and 11, to form a lactate of sodium, potassium, calcium and/or ammonium and magnesium hydroxide, f) separating the lactate of sodium, potassium, calcium and/or ammonium and magnesium hydroxide, and g) recycling the magnesium hydroxide to step b.

The present invention is further illustrated by the following Examples. The Examples merely serve for illustration and should not be construed as being limitative.

EXAMPLES

Example 1

Precipitation of Magnesium Hydroxide from a Magnesium Lactate Containing Solution: Influence of pH A magnesium lactate solution was prepared by dissolving 70 g of magnesium lactate dihydrate per 930 g of demineralised water.

This solution was fed continuously to a 2 L reactor at 50° C. with a flow of 33 ml/min, while maintaining the pH at a certain value by adding sodium hydroxide 50 wt. % solution.

The product slurries obtained at 5 different pH-settings (9.5, 10.0, 10.5, 11.0 and 12.0) were compared. Of every setting a sample of product slurry was taken and allowed to settle. A clear upper layer of sodium lactate solution was obtained, together with a lower layer containing the magnesium hydroxide particles. As the particle size and shape determine the settling properties, a small volume of lower layer is regarded as good. The layer volumes of 25% were still found to be filterable.

| pH | Volume of lower layer (% of original sample volume) |
|---|---|
| 9.5 | 25 |
| 10.0 | 10 |
| 10.5 | 10 |
| 11.0 | 10 |
| 12.0 | 25 |

Example 2

Precipitation of Magnesium Hydroxide from a Magnesium Lactate Containing Solution: Influence of Temperature Example 1 was repeated, but now the pH was fixed at 10.5 and the temperature was varied: 20, 50 and 75° C.

Also filtration speeds, of 250 ml samples of slurry, on a paper filter with vacuum were measured.

The filtration time is the time necessary to separate the slurry into a filter cake and filtrate.

| Temperature (° C.) | Volume of lower layer after sedimentation (% of original sample volume) | Filtration time (s) |
|---|---|---|
| 20 | 6 | 55 |
| 50 | 10 | 40 |
| 75 | 20 | 22 |

So the temperature has a significant influence on the magnesium hydroxide particles formed, resulting in different settling and filtration properties.

The optimal temperature for the reaction of magnesium lactate and sodium hydroxide appeared to be between 20 and 75° C. With a temperature below 20° C. the filtration time becomes relatively long which is not optimal for industrial application whereas temperatures above 75° C. result in a high filtration speed, but large settling volume or filter cake. The best results were obtained at temperatures between 20 and 75° C.

Example 3

Precipitation of Magnesium Hydroxide from a Magnesium Lactate Containing Solution: Influence of Stirring Speed Example 1 at pH=10.5 and temperature 50° C. was repeated with a stirrer speed of 250 rpm instead of 600 rpm.

The volume of the lower layer after settling increased from 10% to 20%. Therefore, intensive stirring is preferred.

Example 4

Precipitation of Magnesium Hydroxide from a Magnesium Lactate Containing Solution: Influence of Ageing Stirring of the product slurry of example 1 at pH=10.5 and temperature 50° C. was continued during one night. The volume of the lower layer after sedimentation increased from 10% to 20%. Therefore, it is preferred to directly separate the magnesium hydroxide from the reaction medium after formation.

Example 5

Precipitation of Magnesium Hydroxide from a Sodium Lactate Containing Slurry

Example 1 at pH=10.5 and temperature 50° C. was repeated, but now different concentrations of magnesium lactate in the feed were used. As the solubility of magnesium lactate is limited, slurries of magnesium lactate were used.

As the concentration of magnesium lactate in the feed varied, also the sodium lactate concentration in the product varied.

The results are compiled in TABLE I.

TABLE I

| Na-lactate concentration (wt. %, in liquid part of slurry) | Filtration time (s) |
|---|---|
| 10.5 | 55 |
| 19.5 | 30 |
| 28.6 | 30-35 |
| 38.7 | 120 |

From TABLE I it is clear that when the concentration of the resulting sodium lactate becomes higher than 30 wt. %, the filtration time increases considerably. This is probably a result of the increased viscosity of the system.

Also, up to 30% the cake after filtration was relatively dry, whereas the cake of the last experiment was rather sticky.

Example 6

Reduction of Residual Magnesium Ions in Sodium Lactate Solutions Obtained

For some further processing techniques the residual magnesium ions in the sodium lactate solution prepared with the process according to the invention should be very low. To this end the resulting magnesium lactate solutions were submitted to a so-called pH adjustment step in a second reactor, i.e. set the pH to 10.5 in the first reactor and to 10.5 or 11.0 in the second reactor with the addition of some NaOH. With said adjustment step the magnesium ion content was reduced from 1600 ppm Mg-ions to 490 and 100 ppm, respectively.

The invention claimed is:

1. Process for the preparation of lactic acid and/or lactate from a medium comprising magnesium lactate, wherein the magnesium lactate is reacted with a hydroxide of sodium, potassium, calcium, and/or ammonium at a pH range between 9.5 and 12 to form a lactate of sodium, potassium, calcium and/or ammonium and magnesium hydroxide.

2. Process according to claim 1, wherein the medium comprising magnesium lactate is pre-treated prior to reacting the magnesium lactate with a hydroxide of sodium, potassium, calcium and/or ammonium.

3. Process according to claim 2, wherein said pre-treatment comprises at least one of biomass separation, washing, re-crystallisation, filtration, concentration, and drying.

4. Process according to claim 1, wherein the magnesium lactate present in the medium is present in the form of a slurry having a magnesium lactate content of up to 38 wt. % (calculated as the anhydrate, based on the total slurry).

5. Process according to claim 1 wherein the magnesium lactate is reacted with a hydroxide of sodium, potassium, calcium and/or ammonium under intensive agitation.

6. Process according to claim 1 wherein the magnesium lactate is reacted with a hydroxide of sodium, potassium, calcium and/or ammonium at a temperature between 20 and 100° C.

7. Process according to claim 1 wherein the magnesium lactate is reacted with a hydroxide of sodium, potassium, calcium and/or ammonium to form sodium, calcium, potassium and/or ammonium lactate in a concentration up to 40 wt. % in the liquid part of the reaction medium.

8. Process according to claim 1 wherein the reaction is carried out continuously.

9. Process according to claim 1 wherein the reaction is carried out in two steps comprising a first step of reacting magnesium lactate with a hydroxide of sodium, potassium, calcium, and/or ammonium at a pH range between 9.5 and 12 to form a lactate of sodium, potassium, calcium and/or ammonium and magnesium hydroxide, and a second step of increasing the pH to between 10.5 to 12.

10. Process according to claim 1 wherein the magnesium hydroxide formed is separated from the reaction medium.

11. Process according to claim 10 wherein the magnesium hydroxide formed is separated directly from the reaction medium after formation.

12. Process according to claim 10 wherein the magnesium hydroxide is washed with water after separation.

13. Process according to claim 10 wherein the resulting magnesium hydroxide is used as a neutralising agent in fermentation of carbohydrates to form lactic acid.

14. Process according to claim 10 wherein the lactate of sodium, potassium, calcium and/or ammonium retrieved after the separation from the magnesium lactate is subjected to a pH correction step.

15. Process according to claim 1 wherein the lactate of sodium, potassium, calcium and/or ammonium is subjected to one or more further purification/modification steps.

16. Process according to claim 15 wherein lactate of sodium, potassium, calcium and/or ammonium is subjected to electrodialysis.

17. Process according to claim 1 wherein the lactate of sodium, potassium, calcium and/or ammonium is converted to lactic acid.

18. Process according to claim 17 wherein the lactate of sodium, potassium, calcium and/or ammonium is converted to lactic acid by bipolar electrodialysis or addition of a strong acid.

19. Process according to claim 1 wherein the medium comprising magnesium lactate originates from the fermentation of carbohydrate.

20. Process according to claim 19, wherein biomass is separated from the medium comprising magnesium lactate prior to reacting the magnesium lactate with a hydroxide of sodium, potassium, calcium and/or ammonium.

21. Process according to claim 20 wherein the biomass is separated by means of filtration and/or sedimentation.

22. Process according to claim 19 wherein magnesium hydroxide is used as a neutralising agent in the fermentation.

23. Process according to claim 22 wherein the magnesium hydroxide used as the neutralising agent is a resulting magnesium hydroxide used as a neutralising agent in fermentation of carbohydrates to form lactic acid, the resulting magnesium hydroxide being separated from the reaction medium, separated directly from the reaction medium after formation, and washed with water after separation.

24. Process according to claim 13 wherein the carbohydrate is sucrose, (liquefied) starch, sugar syrup etcetera.

25. Process for the preparation of lactic acid and/or lactate wherein:
  a) a carbohydrate source is fermented to lactic acid and/or lactate in the presence of a micro-organism,
  b) magnesium hydroxide is used as a neutralising agent during the fermentation,
  c) a medium comprising magnesium lactate is formed,
  d) optionally, the medium comprising magnesium lactate is treated prior to,
  e) reacting magnesium lactate in the medium comprising magnesium lactate with a hydroxide of sodium, potassium, calcium, and/or ammonium at a pH range between 9.5 and 12 to form a lactate of sodium, potassium, calcium and/or ammonium and magnesium hydroxide,
  f) separating the lactate of sodium, potassium, calcium and/or ammonium and magnesium hydroxide, and
  g) recycling the magnesium hydroxide to step b.

26. Process according to claim 1 wherein the hydroxide pH range is between 9.5 and 11.

* * * * *